United States Patent
Yan

(10) Patent No.: US 12,279,755 B2
(45) Date of Patent: Apr. 22, 2025

(54) RIGID ENDOSCOPE

(71) Applicant: ANQING MEDICAL CO., LTD., Shanghai (CN)

(72) Inventor: Hang Yan, Shanghai (CN)

(73) Assignee: ANQING MEDICAL CO., LTD., Shanghai (CN)

(*) Notice: Subject to any disclaimer, the term of this patent is extended or adjusted under 35 U.S.C. 154(b) by 360 days.

(21) Appl. No.: 17/801,256

(22) PCT Filed: Mar. 4, 2020

(86) PCT No.: PCT/CN2020/077826
§ 371 (c)(1),
(2) Date: Aug. 21, 2022

(87) PCT Pub. No.: WO2021/174459
PCT Pub. Date: Sep. 10, 2021

(65) Prior Publication Data
US 2023/0103245 A1    Mar. 30, 2023

(51) Int. Cl.
| | |
|---|---|
| A61B 1/00 | (2006.01) |
| A61B 1/015 | (2006.01) |
| A61B 1/018 | (2006.01) |
| A61B 1/04 | (2006.01) |
| A61B 1/05 | (2006.01) |
| A61B 1/06 | (2006.01) |

(52) U.S. Cl.
CPC ............ *A61B 1/04* (2013.01); *A61B 1/00016* (2013.01); *A61B 1/00103* (2013.01);
(Continued)

(58) Field of Classification Search
CPC ... A61B 1/04; A61B 1/00016; A61B 1/00103; A61B 1/00105; A61B 1/00142;
(Continued)

(56) References Cited

U.S. PATENT DOCUMENTS 6,083,151 A * 7/2000 Renner ............ A61B 1/00135
600/188
2009/0264706 A1 10/2009 Bala
(Continued)

FOREIGN PATENT DOCUMENTS

| CN | 105147229 A | 12/2015 |
|---|---|---|
| CN | 106821286 A | 6/2017 |

(Continued)

OTHER PUBLICATIONS

International Search Report, issued in PCT/CN2020/077826, dated Mar. 4, 2020.
(Continued)

*Primary Examiner* — Timothy J Neal
*Assistant Examiner* — James Edward Boice
(74) *Attorney, Agent, or Firm* — Zhu Lehnhoff LLP

(57) ABSTRACT

The present invention provides a rigid endoscope including a disposable endoscope body structure and a reusable camera assembly. The endoscope body structure includes a handle portion, an endoscope body inserting portion and a line connecting portion, wherein the endoscope body inserting portion is directly or indirectly connected to the handle portion, the line connecting portion includes a receptacle located in the handle portion and an external connecting portion located outside the handle portion, and the receptacle is directly or indirectly connected with the external connecting portion; the handle portion is provided with a camera assembly access port for the camera assembly to access; after accessing and being assembled to the camera assembly access port, the camera assembly access port is able to be inserted into the receptacle to transmit electrical energy and/or a signal with the external connecting portion by using the receptacle.

14 Claims, 5 Drawing Sheets

(52) U.S. Cl.
CPC ...... *A61B 1/00105* (2013.01); *A61B 1/00124* (2013.01); *A61B 1/00142* (2013.01); *A61B 1/015* (2013.01); *A61B 1/018* (2013.01); *A61B 1/05* (2013.01); *A61B 1/0676* (2013.01)

(58) Field of Classification Search
CPC ........... A61B 1/015; A61B 1/018; A61B 1/05; A61B 1/0676
USPC ........................................................ 600/104
See application file for complete search history.

(56) References Cited

U.S. PATENT DOCUMENTS

| | | | | |
|---|---|---|---|---|
| 2015/0164304 | A1* | 6/2015 | Sakata | A61B 1/0008 600/140 |
| 2016/0242799 | A1* | 8/2016 | Bonneau | A61B 1/05 |
| 2017/0007103 | A1* | 1/2017 | Hashiguchi | A61B 1/018 |
| 2019/0246884 | A1* | 8/2019 | Lu | A61B 1/018 |
| 2019/0282073 | A1* | 9/2019 | Truckai | A61B 1/00179 |
| 2021/0219816 | A1* | 7/2021 | Truckai | A61B 1/00009 |

FOREIGN PATENT DOCUMENTS

| | | |
|---|---|---|
| CN | 107049215 A | 8/2017 |
| CN | 109310408 A | 2/2019 |
| CN | 110013299 A | 7/2019 |
| CN | 110215180 A | 9/2019 |
| CN | 110251057 A | 9/2019 |

OTHER PUBLICATIONS

Written Opinion, issued in PCT/CN2020/077826, dated Mar. 4, 2020.

* cited by examiner

RIGID ENDOSCOPE

TECHNICAL FIELD

The present invention relates to an endoscope, in particular, to a rigid endoscope.

BACKGROUND

In recent years, endoscopes and related surgical instruments are used extensively in the field of minimally invasive diagnosis and treatment. With the rapid development of minimally invasive medical technology, higher requirements are put forward for endoscopes. According to the sites at which the endoscope arrives, the endoscope can be classified into a neural endoscope, a cysto-urethroscope, a resectoscope, a laparoscope, an arthroscope, a nasal endoscope, a laryngoscope, and so on. According to the bending degree of the head of the endoscope, the endoscope can be divided into a flexible bendable endoscope and a rigid endoscope. The endoscope structure can be reusable.

Medical products, especially those related products contacting with the blood and the mucous membrane tissues, have very strong requirements for single use. At home and abroad, there are many designs of sleeving a layer of leather or a cover on reusable endoscope. This similar design has several problems: 1. It will increase the outer diameter of the endoscope; 2. Dismantling is complex and there is a risk of sterile cross-contamination; 3. Sleeving the leather on the inserting portion alone cannot achieve complete sterile isolation from the handle. 4. Sleeving the leather on the entire endoscope may severely influence the operations of use; 5. Reflections from the lighting of the external leather may produce interfering imaging. 6. The external leather may affect the bending angle of the endoscope, and so on.

Since the reusable endoscope may contact the patients and the medical personnel, it needs to be sterilized, disinfected, etc. However, due to the complexity of the endoscope, elements therein such as camera, light source component, and medical-related device are generally encapsulated by an encapsulation glue to form an encapsulation structure. After being subjected to moist heat sterilization many times, the encapsulation glue is prone to destabilizing its structure so that the structure of the encapsulation structure and the endoscope structure is caused to be no longer stable, and there will be internal leakage that makes the sterilization effect undesirable.

In view of this, the endoscope can be configured to be reusable and to be accessed by a disposable structure. Meanwhile, electrical wires should be configured to transmit electrical energy and signals at the rear end of the endoscope, and a sterilization sheath should be connected with the rear end of the endoscope. It can be seen that although the endoscope is isolated, the electrical wires used therewith are not completely isolated; since the endoscope is not completely encased, which can still cause safety hazards as well as complexity in usage. In addition, it should be further noted that viruses such as the novel coronavirus are highly contagious and cause many cases of infection or cases of pending diagnosis, so that countries cannot afford the cost for disposable electronic endoscopes; reusable endoscopes fail to guarantee security when facing such a strong infectious virus; the method of sleeving a layer of leather or cover on a reusable endoscope is expensive and lacks the equipment. This type of endoscope not only takes longer time in manufacturing process but also causes inconvenience in use, tremendously compromising medical safety. Therefore, there is still a need for new products with technological advances.

SUMMARY

The present invention provides a rigid endoscope to solve security risks of no sterile isolation and problems of being not easy to operate due to excessive parts during the assembly.

According to a first aspect of the present invention, a rigid endoscope is provided including a disposable endoscope body structure and a reusable camera assembly, wherein the endoscope body structure includes a handle portion, an endoscope body inserting portion and a line connecting portion; the endoscope body inserting portion is directly or indirectly connected to the handle portion, the line connecting portion includes a receptacle located in the handle portion and an external connecting portion located outside the handle portion, and the receptacle is directly or indirectly connected with the external connecting portion;

the handle portion is provided with a camera assembly access port for the camera assembly to access; after accessing and being assembled to the camera assembly access port, the camera assembly access port is able to be inserted into the receptacle to transmit electrical energy and/or a signal with the external connecting portion by using the receptacle.

Optionally, the camera assembly includes a camera, a conducting rod, a grip, a male connector disposed at the grip, and a first electrical wire;

one end of the conducting rod is connected with the grip, and the camera is disposed at the other end of the conducting rod; the electrical wire penetrates through the conducting rod and the grip, one end of the first electrical wire is directly or indirectly connected with the camera, and the other end of the first electrical wire is directly or indirectly connected with the male connector;

after the camera assembly accesses and is assembled to the camera assembly access port, the male connector is inserted into the receptacle, and the conducting rod penetrates through the endoscope body inserting portion.

Optionally, the grip includes a grip head and an elastic compensation structure disposed at the grip head, one end of the elastic compensation structure along a length direction of the conducting rod is directly or indirectly connected with the conducting rod, and the other end of the elastic compensation structure along the length direction of the conducting rod is directly or indirectly connected with the grip head, the grip head being fixed relative to the handle portion after the camera assembly accesses and is assembled to the camera assembly access port;

the elastic compensation structure is configured to directly or indirectly push the conducting rod by using an elastic force after the camera assembly accesses and is assembled to the camera assembly access port, so that the camera is located at a tip of the endoscope body inserting portion.

Optionally, the elastic compensation structure includes an elastic component, a component cover and a component sleeve, a side wall of the grip head close to the camera being provided with an elastic-component through hole, and the elastic component, the component cover and the component sleeve being all disposed in an inner cavity of the grip head, and the elastic component being connected between the component cover and the component sleeve along the length direction of the conducting rod;

the first electrical wire penetrates through the elastic-component through hole, the component cover and the component sleeve in sequence, the component sleeve is fixed relative to the conducting rod, and the component cover is fixed relative to the grip.

Optionally, the elastic compensation structure further includes a component seat, the component seat penetrating through the elastic-component through hole, the component cover and the elastic component both being located at an inner side of the component seat, and the component cover covering an end of the component seat deviated from a camera encapsulation portion.

Optionally, the component seat includes a flat seat body and a cylinder seat body, and an end of the flat seat body being connected with the cylinder seat body; the flat seat body being located outside the grip head, the cylinder seat body penetrating through the elastic-component through hole, and a shape of an outer wall of the cylinder seat body being matched with an inner wall of the elastic-component through hole.

Optionally, the male connector and the elastic-component through hole are disposed at the same side wall of the grip head, and an inner cavity of the grip head is further provided with a male connector circuit board; the male connector circuit board being fixed relative to the side wall, and the first electrical wire being connected with the male connector via the male connector circuit board.

Optionally, the male connector is a Type C male connector, and the receptacle is a Type C receptacle.

Optionally, the endoscope body structure further includes a passage tube and a guider that are fixedly connected to the handle portion, the passage tube penetrating through the handle portion, the endoscope body inserting portion being connected to one end of the passage tube, and the guider being connected to the other end of the passage tube;

after the camera assembly accesses and is assembled to the camera assembly access port, the grip accesses the guider, and the conducting rod penetrates through the passage tube and the endoscope body inserting portion in sequence.

Optionally, the rigid endoscope further includes a sterile isolation cover, wherein the sterile isolation cover is configured to cover the camera assembly access port after the camera assembly accesses and is assembled to the camera assembly access port.

Optionally, the endoscope body inserting portion includes an inserting rod and a head module, the head module being disposed at a tip of the inserting rod, and the other end of the inserting rod being connected with the handle portion;

the head module is provided with a light transmission sheet and an illumination module, and the camera assembly accessing the endoscope body inserting portion may collect images externally through the light transmission sheet.

Optionally, the inserting rod is internally provided with a camera passage, an instrument passage and a liquid tube passage, a camera through hole, an instrument through hole and a liquid tube through hole penetrating through the head module; the camera passage is connected to one end of the camera through hole, the light transmission sheet is disposed at a tip of the camera through hole, the instrument passage is connected to one end of the instrument through hole, and the liquid tube passage is connected to one end of the liquid tube through hole;

the handle portion is provided with an instrument access port for accessing an instrument and a liquid port, the liquid port being communicated to the liquid passage, and the liquid portion being provided with a water valve.

Optionally, a material of the conducting rod is a shape memory alloy material.

Optionally the line connecting portion further includes a receptacle circuit board and a second electrical wire, the receptacle circuit board being electrically connected with the receptacle, and the receptacle circuit board is connected with the external connecting portion via the second electrical wire to transmit the electrical energy and/or the signal by using the second electrical wire; the receptacle circuit board being located in the handle portion, and the second electrical wire penetrating through a wire via disposed at the handle portion.

Optionally, the external connecting portion is a wired connecting receptacle or a wireless communication component.

The rigid endoscope provided by the present invention includes the disposable endoscope structure and the reusable camera assembly, and an electrical connection externally may be performed by the receptacle of the endoscope structure and the external connecting portion after the camera assembly accesses the camera assembly access port of the endoscope structure, so that the camera assembly itself may not be directly electrically connected externally and further the camera assembly in the present invention may be completely isolated sterilely, thereby effectively avoiding or reducing the security risks; since the electrical wire of the camera assembly is not required to pass through the sterile sheath (while the sterile isolation cover may not be a necessity), the difficulty in operation is further reduced, thereby facilitating the use, the disassembly and disposable discarding.

In addition, according to the present invention, the electrical connection may be achieved by inserting the male connector with the receptacle, so that a positive effect of simple assembly may be generated; meanwhile, the disposable use and discarding of the receptacle and the external connecting portion as a whole may further generate a positive effect of facilitating the overall disposal.

It can be seen that with the solution involved in the present invention, medical scenes where the novel coronavirus, other seriously contagious virus and the like exist may be met, thereby effectively guaranteeing the security and facilitating the use and disposal.

In the further optional solution, based on the structure of resilience compensation, the encapsulation portion of the camera may be located at a required position by using the elastic force, thereby eliminating the effect caused by dimensional errors in manufacturing and assembly on the camera.

BRIEF DESCRIPTION OF THE DRAWINGS

To describe the technical solutions in the embodiments of the present invention or in the prior art more clearly, accompanying drawings required to describe the embodiments or the prior art are briefly described below. It is obvious that the accompanying drawings described below are only some embodiments of the present invention. It is apparent to those of ordinary skill in the art that other drawings may be further obtained based on the accompanying drawings without inventive effort.

DESCRIPTION OF REFERENCE NUMERALS

1—endoscope body structure;
11—endoscope body inserting portion;
111—inserting rod;
1111—instrument tube;
1112—liquid tube;
1113—illumination electrical wire;
112—head module;
1121—light transmission sheet;
1122—illumination module;
1123—illumination circuit board;
1124—instrument through hole;
1125—liquid through hole;
12—line connecting portion;
121—receptacle;
122—external connecting portion;
123—second electrical wire;
124—receptacle circuit board;
13—handle portion;
131—camera assembly access port;
132—instrument access port;
133—liquid port;
14—passage tube;
15—guider;
16—fixing seat;
2—camera assembly;
21—grip;
211—grip head;
212—elastic compensation structure;
2121—elastic component;
2122—component cover;
2123—component sleeve;
2124—component seat;
21241—flat seat body;
21242—cylinder seat body;
2125—sealing ring;
22—male connector;
23—camera encapsulation portion;
24—conducting rod;
25—first electrical wire;
26—male connector circuit board;
3—sterile isolation cover;
4—instrument mouth;
5—water valve.

DETAILED DESCRIPTION OF THE EMBODIMENTS

Clear and intact descriptions will be made on technical schemes in the embodiments of the present invention below in combination with drawings in the embodiments of the present invention. Obviously, the described embodiments are merely a part of embodiments of the present invention and are not all the embodiments. Based on the embodiments of the present invention, all the other embodiments obtained by those of ordinary skill in the art without inventive effort are within the scope of the present invention.

Terms "first", "second", "third", "fourth", and the like (if any) in the specification and claims of the present invention and the foregoing accompanying drawings are used to distinguish similar objects, but do not need to be used for describing a specific sequence or an order. It should be understood that data used in this way can be interchanged under appropriate circumstances, so that the embodiments of the present invention described herein can be implemented in an order other than those illustrated or described herein. In addition, terms "including", "having", and any variations thereof are intended to cover non-exclusive inclusions, for example, processes, methods, systems, products, or devices that contain a series of steps or units need not be limited to those clearly listed steps or units, but may include other steps or units not explicitly listed or inherent to these processes, methods, products, or devices.

The technical solutions of the present invention are described in detail below with reference to the specific embodiments. The following several embodiments may be combined with each other, and a same or similar concept or process may not be described again in some embodiments.

Figure 1:
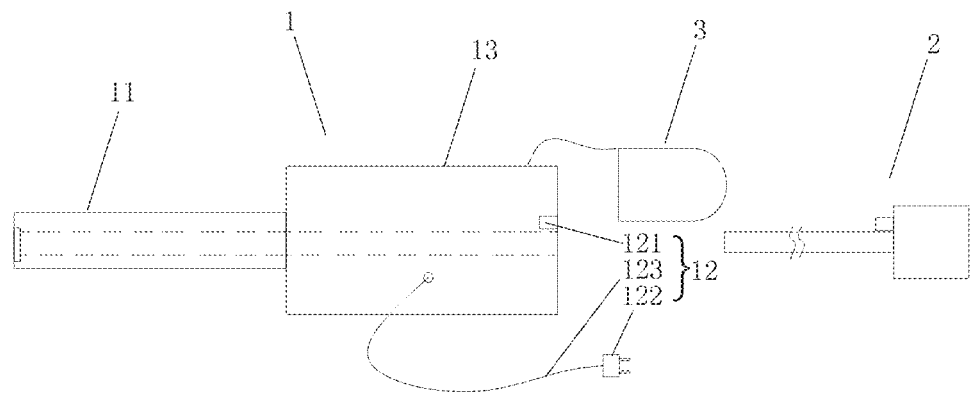
FIG. 1 is a construct diagram of a rigid endoscope according to an embodiment of the present invention.
Figure 2:
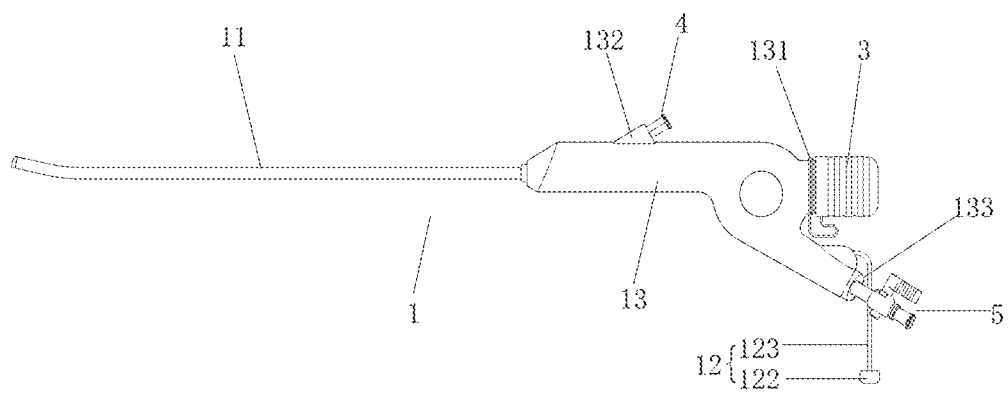
FIG. 2 is a structural diagram of the rigid endoscope according to an embodiment of the present invention.

FIG. 1 is a construct diagram of a rigid endoscope according to an embodiment of the present invention; FIG. 2 is a structural diagram of the rigid endoscope according to an embodiment of the present invention.

With reference to FIGS. 1 and 2, a rigid endoscope includes a disposable endoscope body structure 1 and a camera assembly 2 capable of being reusable. The endoscope body structure 1 may be a sterile product, which may be discarded after being used; the camera assembly 2 should be disinfected (in the form of alcohol wipe or plasma sterilization) before the operation is carried out.

The endoscope body structure 1 includes a handle portion 13, an endoscope body inserting portion 11 and a line connecting portion 12.

The endoscope body inserting portion 11 is directly or indirectly connected to the handle portion 13, the line connecting portion 12 includes a receptacle 121 located in the handle portion 13 and an external connecting portion 122 located outside the handle portion 13, the receptacle 121 being directly or indirectly connected with the external connecting portion 122 such as by way of a circuit board, an electrical wire and the like. With the external connecting portion 122, the electrical connection with other equipment may be achieved, e.g., being electrically connected with a host, and further, a signal is processed by the host to be imaged on display.

The handle portion 13 is provided with a camera assembly access port 131 for the camera assembly 2 to access typically in a linear direction; after the camera assembly 2 accesses and is assembled to the camera assembly access port 131, it is able to be inserted into the receptacle 121 to transmit electrical energy and/or a signal with the external connecting portion 122 by using the receptacle 121.

The endoscope body structure 1 may be understood to be configured with the receptacle 121 and the external connecting portion 122, and may be any structure that can provide an isolated environment for the accessed camera assembly 2. Also, the endoscope body structure may be described as an endoscope, an outer sheath and the like, and any construct that is applied to the endoscope body, the endoscope sheath and the outer sheath may be applied to the present embodiment for realizing the functions of the endoscope body structure 1.

The camera assembly 2 may be understood to be configured with the male connector and the camera encapsulation portion, and may be any structure that can realize endoscopy through the image acquisition.

A structure state where the camera assembly 2 involved above is assembled to the camera assembly access port 131 may be understood as a structure state where the camera assembly 2 accesses and reaches a desired position, and may also be understood as a structure state where the sterile isolation cover 3 has been assembled in case of using the sterile isolation cover 3.

The transmission of electrical energy involved above may, for example, power the camera encapsulation portion in the camera assembly 2; in a specific example, the transmission of electrical energy also does not exclude the means of powering the lighting modules, etc.; the transmission of the signal involved above may be, for example, the transmission of signals of CMOS images, or, for example, the transmission of control signals of the camera encapsulation portion.

Figure 3:
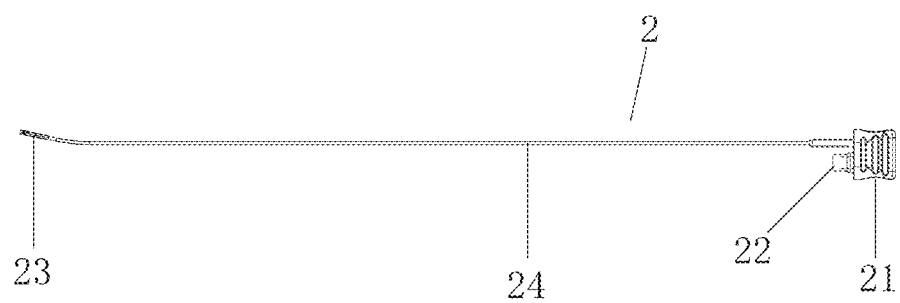
FIG. 3 is a structural diagram one of a camera assembly according to an embodiment of the present invention.
Figure 4:
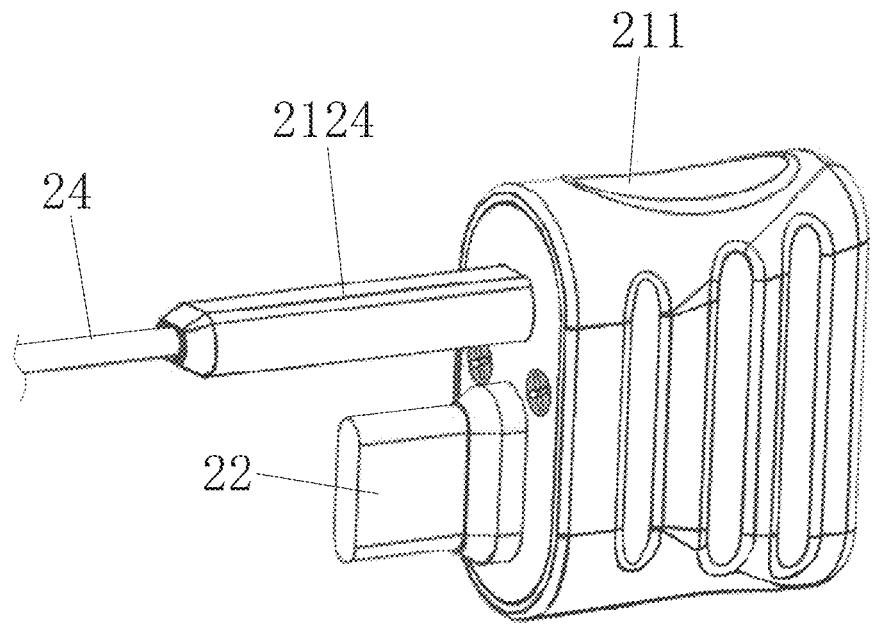
FIG. 4 is a partial structural diagram one of the camera assembly according to an embodiment of the present invention.
Figure 5:
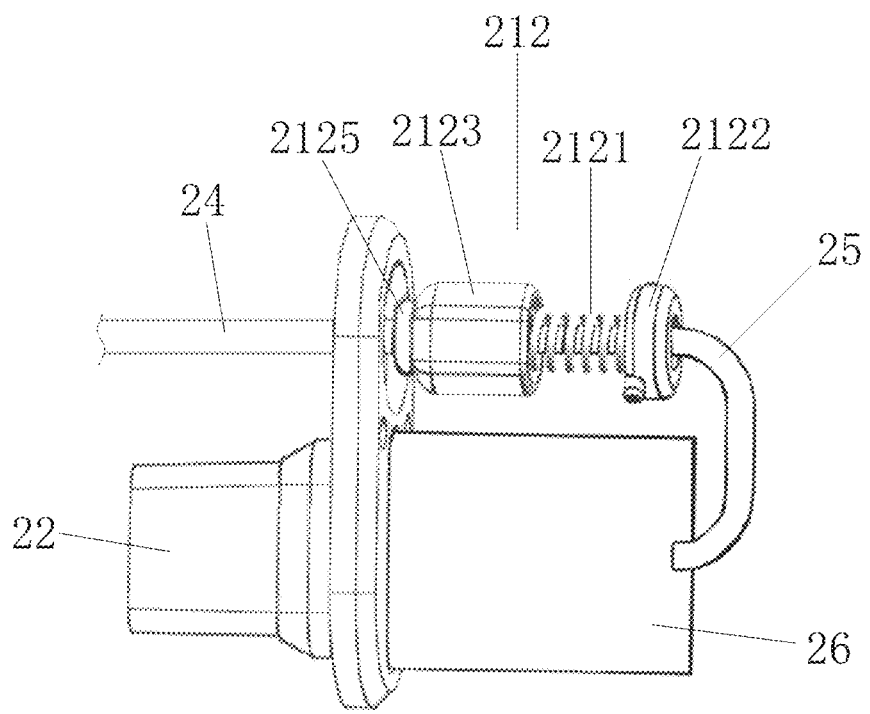
FIG. 5 is a partial structural diagram two of the camera assembly according to an embodiment of the present invention.
Figure 6:
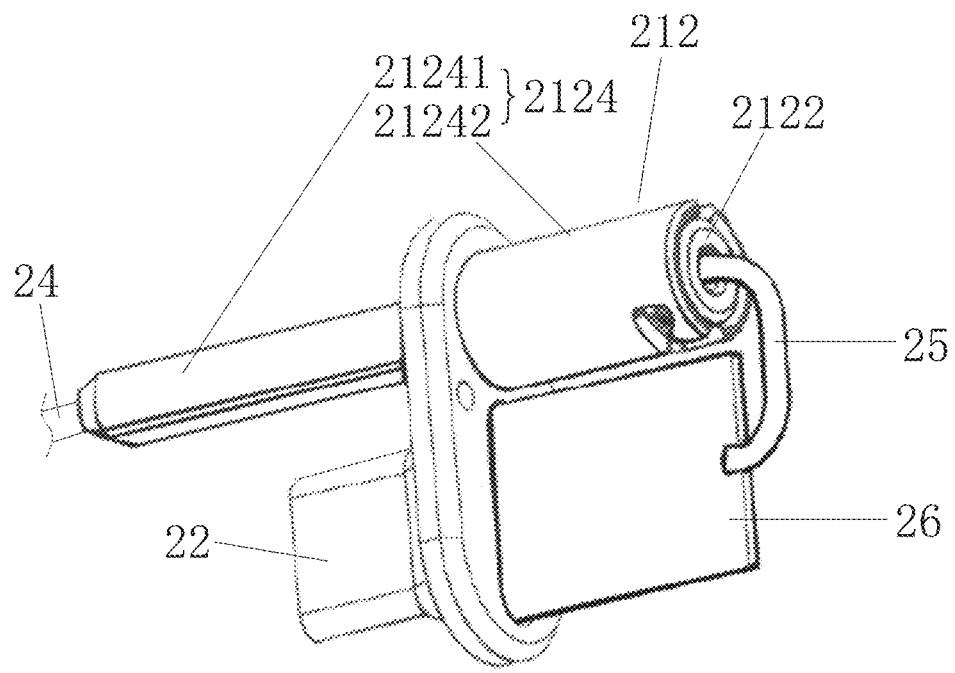
FIG. 6 is a partial structural diagram three of the camera assembly according to an embodiment of the present invention.

As can be seen, in the above solutions of the present embodiment, the electrical connection may be performed externally by the receptacle of the endoscope body structure and the external connecting portion after the camera assembly accesses the camera assembly access port of the endoscope body structure, so that the camera assembly itself may not be directly electrically connected externally and further the camera assembly in the present embodiment may be completely isolated sterilely, thereby effectively avoiding or reducing the security risks; meanwhile, since the electrical wire of the camera assembly is not required to pass through the sterile sheath, the difficulty in operation is further reduced. FIG. 3 is a structural diagram one of a camera assembly according to an embodiment of the present invention; FIG. 4 is a partial structural diagram one of the camera assembly according to an embodiment of the present invention; FIG. 5 is a partial structural diagram two of the camera assembly according to an embodiment of the present invention; FIG. 6 is a partial structural diagram three of the camera assembly according to an embodiment of the present invention.

With reference to FIGS. 3 to 6, the camera assembly 2 may include a camera encapsulation portion 23, a conducting rod 24, a grip 21, a male connector 22 disposed at the grip 21 and a first electrical wire 25.

One end of the conducting rod 24 is connected with the grip 21 by way of direct connection or indirect connection, and the camera encapsulation portion 23 is disposed at the other end of the conducting rod 24; the first electrical wire 25 penetrates through the conducting rod 24 and the grip 21, one end of the first electrical wire 25 is directly or indirectly connected with the camera encapsulation portion 23, and the other end of the first electrical wire is directly or indirectly connected with the male connector 22.

The first electrical wire may refer to a single electrical wire, and may also include a plurality of same or different electrical wires; meanwhile, a solution where other devices are configured in the electrical wire may not excluded.

After the camera assembly 2 accesses and is assembled to the camera assembly access port 131, the male connector 22 is inserted into the receptacle 121, and the conducting rod 24 penetrates through the endoscope body inserting portion 11.

In an embodiment, in the process of manufacturing the disposal endoscope body structure, lengths of the endoscope body inserting portion 11 and the camera passage thereof are difficult to control accurately.

Therefore, the camera encapsulation portion 23 may be difficult to reach the pre-set position, e.g., may be difficult to accurately reach the tip of the endoscope body inserting portion 11 to capture the image in front, which further directly affects or decreases the field-of-view angle size of the image and reduces the field of view. Thus, in the present embodiment, an elastic compensation structure 212 is further introduced; specifically, the grip 21 includes a grip head 211 and the elastic compensation structure 212 disposed at the grip head 211.

One end of the elastic compensation structure 212 along an access direction of the camera assembly (may also be understood as a length direction of the conducting rod 24) is directly or indirectly connected with the conducting rod 24, and the other end of the elastic compensation structure is directly or indirectly connected with the grip head 211, e.g., connected to the grip head 211 via a component cover 2122, so as to further realize the relative fixation of the positions. The grip head 211 is fixed relative to the handle portion 13 after the camera assembly 2 accesses and is assembled to the camera assembly access port 131; for example, a corresponding positioning structure may be configured in the handle portion 13, and the grip head 211 may be fixed to a position relative to the handle portion 13 through the positioning structure after being accessed.

The elastic compensation structure 212 is configured to directly or indirectly push the conducting rod 24 by using an elastic force after the camera assembly 2 accesses and is assembled to the camera assembly access port 131, so that the camera encapsulation portion 23 is located at a tip of the endoscope body inserting portion, or may be understood to be located at the required position.

The elastic force produced by the elastic compensation structure 212 may be a force produced by a force deformation of the elastic component to overcome the deformation. If the elastic component is a spring, the deformation may be, for example, a stretch or a compression; or if the elastic component is an elastic sheet or other constructs, the deformation may also be the movement of a part of components in the construction.

In actual implementation, the elastic compensation structure 212 includes an elastic component 2121 (e.g., a spring), a component cover 2122 and a component sleeve 2123, and a side wall of the grip head 211 close to the camera encapsulation portion (i.e., the side wall on the right of FIG. 4) is provided with an elastic-component through hole, wherein the elastic-component through hole may be used for a part of constructs in the elastic compensation structure 212 to penetrate through, and the elastic component 2121, the component cover 2122 and the component sleeve 2123 are all disposed in an inner cavity of the grip head 211; the elastic component 2121 is connected between the component cover 2122 and the component sleeve 2123 along the access direction (i.e., the linear direction in which the camera assembly 2 accesses the camera assembly access port 131, or the length direction of the conduction rod 24).

The first electrical wire 25 penetrates through the elastic-component through hole, the component sleeve 2123, and the component cover 2122 in sequence. As exemplified in FIG. 4, the first electrical wire 25 may pass through the elastic-component through hole, the component sleeve, and the component cover in sequence from right to left. The component sleeve 2123 is fixed relative to the conducting rod 24, e.g., may be fixedly connected to the latter by welding; the component cover 2122 is fixed relative to the grip head 211, e.g., may be fixedly connected to the latter directly or indirectly.

In actual implementation, with reference to FIG. 6, the elastic compensation structure 212 further includes a component seat 2124, the component seat penetrating through the elastic-component through hole, the component cover 2123 and the elastic component 2121 both being located at an inner side of the component seat 2124, and the component cover 2122 covering an end of the component seat 2124 deviated from a camera encapsulation portion 23; further, the component cover 2122 is fixed relative to the component seat 2124, and the component seat 2124 is fixed relative to the grip head 211.

In a further example, with reference to FIG. 6, the component seat 2124 includes a flat seat body 21241 and a cylinder seat body 21242, and an end of the flat seat body 21241 being connected with the cylinder seat body 21242; the flat seat body 21241 being located outside the grip head, the cylinder seat body 21242 penetrating through the elastic-component through hole, and a shape of an outer wall of the cylinder seat body 21242 being matched with an inner wall of the elastic-component through hole. The cylinder seat body 21242 may be integral with the flat seat body 21241, and the two may be assembled as a whole. Through the flat shape at the front end, guiding functions may be exerted when the disposable endoscope body is inserted.

In addition, in a specific example, the elastic compensation structure 212 further includes a sealing ring 2125 provided at one end of a docking side wall disposed at the component sleeve 2123, which may be used to prevent the liquid from entering in a non-working state.

With the above solution, based on the structure of resilience compensation, the encapsulation portion of the camera may be located at a required position by using the elastic force, thereby eliminating the effect caused by dimensional errors in manufacturing and assembly on the camera.

In a specific implementation process, the male connector 22 and the elastic-component through hole are disposed at the same side wall of the grip head, and further accessing the grip head and docking the male connector with the receptacle may be achieved by an accessing movement in the same direction.

The inner cavity of the grip head 211 is further provided with a male connector circuit board 26; the male connector circuit board 26 is fixed relative to the side wall, and the first electrical wire 25 is connected with the male connector 22 via the male connector circuit board 26. In the above solution, the electrical connection is achieved based on the circuit board, so that the stability of the electrical connection may be effectively guaranteed.

In a specific implementation process, the male connector 22 may be a Type C male connector, and correspondingly, the receptacle 121 may be a Type C receptacle. In other examples, a male connector and a receptacle that are of A type may be included, or other male connectors and receptacles based on USB may be included. The present embodiment does not exclude the male connectors and the receptacles based on other protocols and constructs.

In view of this, according to the present embodiment, the electrical connection may be achieved by inserting the male connector with the receptacle, so that a positive effect of simple assembly may be generated; meanwhile, the disposable use and discarding of the receptacle and the external connecting portion may further generate a positive effect of facilitating the overall disposal.

In a specific implementation process, a material of the conducting rod 24 is a shape memory alloy material, e.g., may be a nickel-titanium alloy. The memorized shape allows for easy bending and access.

Figure 7:
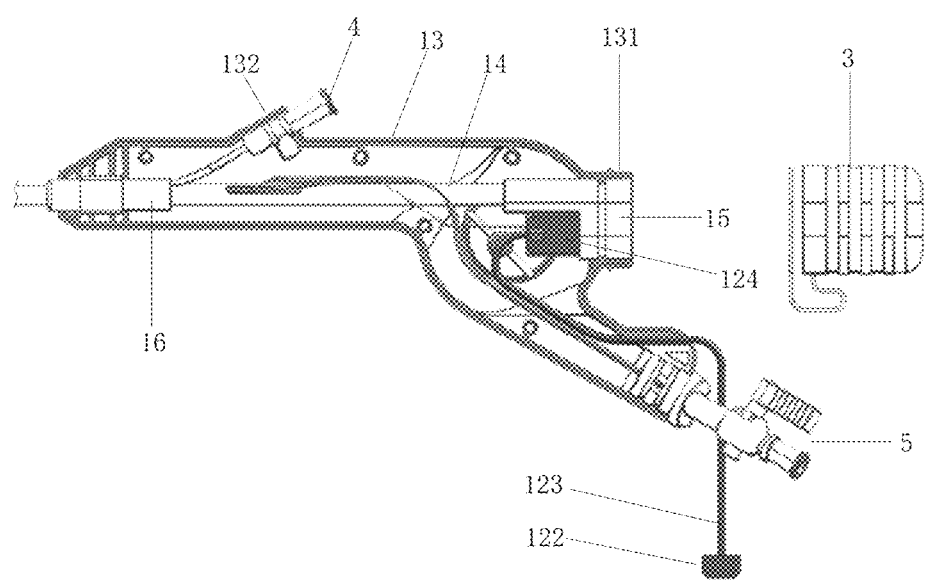
FIG. 7 is a partial structural diagram of the rigid endoscope according to an embodiment of the present invention.

FIG. 7 is a partial structural diagram of the rigid endoscope according to an embodiment of the present invention.

In a specific implementation process, with reference to FIG. 7, the endoscope body structure 1 further includes a passage tube 14 fixedly connected with the handle portion 13 and a guider 15, wherein the passage tube 14 penetrates through the handle portion 13, the endoscope body inserting portion 11 is connected to one end of the passage tube 14 (e.g., the left end of FIG. 7), and the guider 15 is connected to the other end of the passage tube 14 (e.g., the right end of FIG. 7).

The endoscope body inserting portion 11 may be integral with the passage tube 14, and then the passage tube 14 may also be considered a part of an inserting rod 111 of the endoscope body inserting portion 11; in other examples, the endoscope body inserting portion 11 and the passage tube 14 may be assembled with each other or connected with each other by a certain process.

After the camera assembly 2 accesses and is assembled to the camera assembly access port 131, the grip 21 accesses the guider 15, and the conducting rod 24 penetrates through the passage tube 14 and the endoscope body inserting portion 11 (e.g., the inserting rod 111 thereof) in sequence. Meanwhile, the receptacle may also be disposed in the guider 15, and the guiding function may be exerted for inserting the camera portion that is reusable by the guider 15.

In a specific implementation process, the passage tube 14 may be fixedly connected in the handle portion 13 through the fixing seat 16, and correspondingly the handle portion 13 may be internally provided with a construct matched with the fixing seat 16. Further, through the fixing seat, it is easy for controlling the direction and the length of the endoscope body inserting portion 11 (e.g., the inserting rod 111 thereof) and the passage tube 14 to limit the positions of the instrument tube, the liquid tube and the electrical wires and the like in the endoscope body inserting portion 11 (e.g., the inserting rod 111 thereof).

In a specific implementation process, with reference to FIG. 7, the line connecting portion 12 further includes a receptacle circuit board 124 and a second electrical wire 123, the receptacle circuit board 124 being electrically connected with the receptacle, and the receptacle circuit board is connected with the external connecting portion 122 via the second electrical wire 123 to transmit the electrical energy and/or the signal by using the second electrical wire 123; the receptacle circuit board 124 being located in the handle portion 13, and the second electrical wire 123 penetrating through a wire via disposed at the handle portion.

It can be seen that a path for transmitting the electrical energy and/or the signal may be formed among the camera encapsulation portion 23, the first electrical wire 25, the male connector 22, the receptacle 121, the second electrical wire 123 and the external connecting portion 122.

In addition, in the above solution, the receptacle 121 is wiredly connected with the external connecting portion 122, and the external connecting portion 122 is wiredly connected with the external equipment (e.g., a host); in other optional solutions, if the transmission of signals is required, the receptacle may also be wirelessly connected with the external connection portion, and the external connecting portion may also be wirelessly connected with the external equipment (e.g., the host). It can be seen that the external connecting portion 122 may be a wired connecting receptacle or a wireless communication component.

Figure 8:
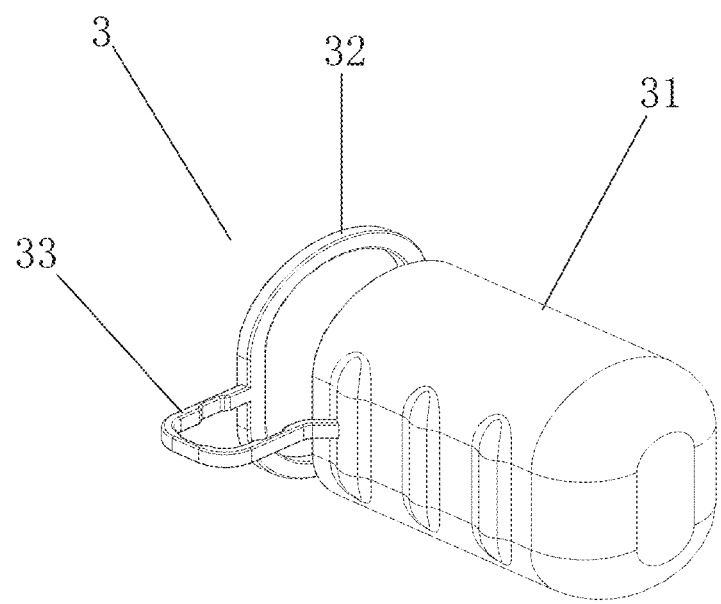
FIG. 8 is a structural diagram of a sterile isolation cover according to an embodiment of the present invention.

FIG. 8 is a structural diagram of a handle portion according to an embodiment of the present invention.

With reference to FIGS. 8, 2 and 7, the flexible endoscope further includes a sterile isolation cover 3, wherein the sterile isolation cover 3 is configured to cover the camera assembly access port 131 after the camera assembly 2 accesses and is assembled to the camera assembly access port 131. Through the sterile isolation cover, the endoscope body structure 1 may be isolated internally.

Taking FIG. 8 as an example, the sterile isolation cover 3 may include an isolation cover body 31, a connecting tape 33 and a mounting ring 32, wherein the mounting ring 32 may be connected to the endoscope body structure 1 (e.g., the handle portion 13 thereof), and the isolation cover body 31 may be connected with the mounting ring 32 through the connecting tape 33.

In the implementation process, the camera assembly 2 is able to be inserted into the endoscope body structure 1, and then the power supply of the camera portion 2 and the transmission of the CMOS images may be completed by connecting the line connecting portion 12 with a suitable host. After the camera assembly 2 is inserted into the endoscope body structure 1, the sterile isolation cover 3 may be buckled to a tail of the endoscope body portion 1, so that non-sterilized components are completely isolated from doctors and patients.

In other optional solutions, the detachable sterile isolation cover 3 may not be adopted; for example, the camera assembly 2 may be directly disposed into the endoscope body structure 1, so that the external endoscope body structure 1 may be directly discarded without implementing corresponding detaching processes when the disposal is required. Further, the disassembly and disposal may be facilitated, which causes positive technical effects such as saving the time for assembly.

Figure 9:
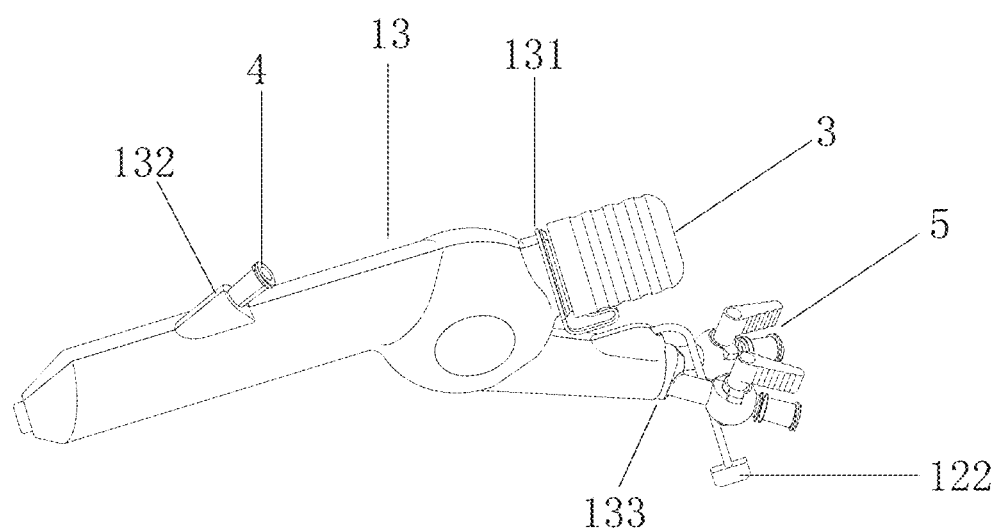
FIG. 9 is a structural diagram of a handle portion according to an embodiment of the present invention.
Figure 10:
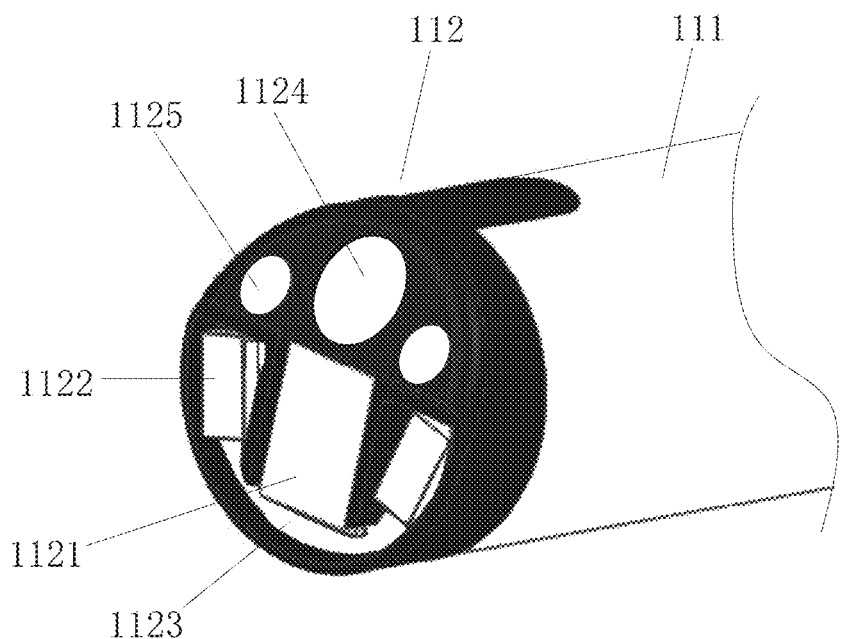
FIG. 10 is a structural diagram of a head module according to an embodiment of the present invention.
Figure 11:
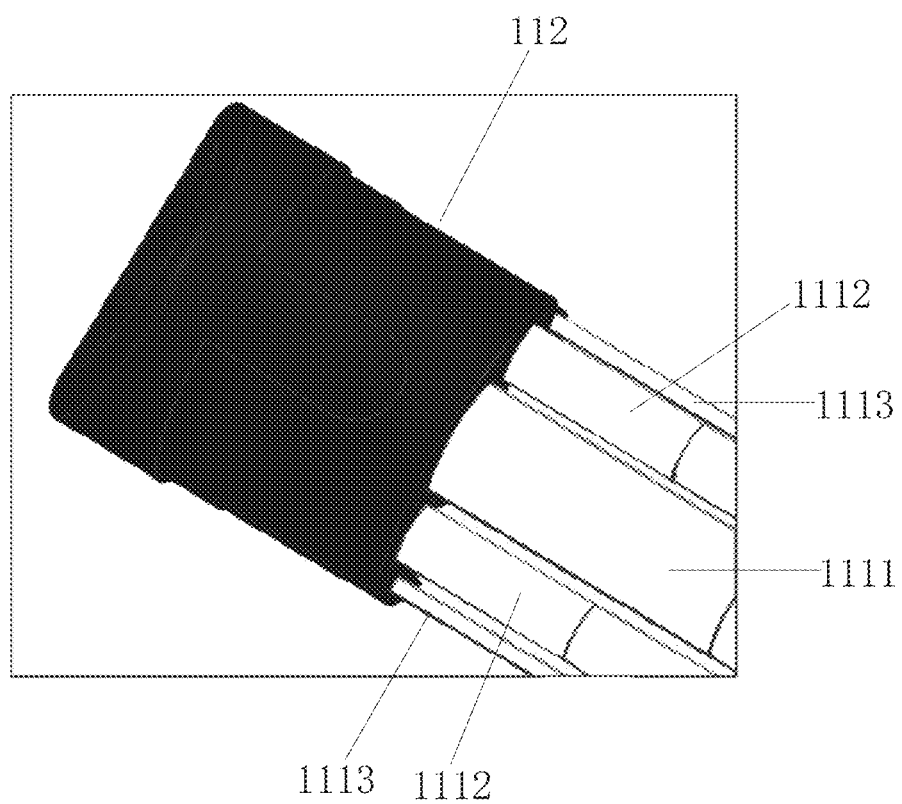
FIG. 11 is a structural diagram of an instrument tube, a liquid tube and the head module according to an embodiment of the present invention.

FIG. 9 is a structural diagram of a handle portion according to an embodiment of the present invention; FIG. 10 is a structural diagram of a head module according to an embodiment of the present invention; FIG. 11 is a structural diagram of an instrument tube, a liquid tube and the head module according to an embodiment of the present invention.

With reference to FIGS. 9 to 11, the endoscope body inserting portion 11 includes an inserting rod 111 and a head module 112, the head module 112 being disposed at one end of the inserting rod 111, and the other end of the inserting rod 111 being connected with the handle portion 13, e.g., through the passage tube 14;

the head module 112 is provided with a light transmission sheet 1121 and an illumination module 1122, and the camera assembly accessing the endoscope body inserting portion may collect images externally through the light transmission sheet 1121.

The light transmission sheet 1121 may be, for example, a glass sheet.

With reference to FIG. 11, the inserting rod 111 may be internally provided with a camera passage (not shown), an instrument passage (e.g., a passage formed in the instrument tube 1111) and a liquid passage (e.g., a passage formed in the liquid tube 1112), a camera through hole (e.g., a through hole behind the light transmission sheet), an instrument through hole 1124 and a liquid tube through hole 1125 penetrating through the head module 112; the camera passage is connected to one end of the camera through hole, the light transmission sheet is disposed at the other end of the camera through hole, the instrument passage is connected to one end of the instrument through hole, and the liquid passage is connected to one end of the liquid tube through hole;

the handle portion is provided with an instrument access port 132 for accessing an instrument and a liquid port 133, wherein the liquid port 133 is communicated to the liquid passage; for example, the liquid tube 1113 may be exported from the inserting rod 111 and communicated to the liquid port 133. The liquid port 133 is provided with a water valve 5, and the instrument access port 132 may be provided with an instrument mouth 4 that may be communicated with the instrument passage, so that further the instrument may enter the instrument passage via the instrument mouth 4.

The illumination module 1122 may be, for example, an LED module, which may be disposed at the circuit board 1123, the circuit board 1123 being capable of being disposed at the head module 112.

In a specific implementation process, in order to power the illumination module 1122, the inserting rod 111 may further be internally provided with an illumination electrical wire 1113, which may be directly or indirectly connected to the line connecting portion 12 (e.g., the receptacle 121), thereby achieving the power supply and/or control of the illumination module 1122.

For the inserting rod and the head module involved above, any existing or improved construction in the art may be used, without departing from the description of the present embodiment.

In summary, according to the rigid endoscope provided by the present embodiment, the disposable endoscope body structure and the reusable camera assembly may be included, wherein an electrical connection externally may be performed by the receptacle of the endoscope structure and the external connecting portion after the camera assembly accesses the camera assembly access port of the endoscope structure, so that the camera assembly itself may not be directly electrically connected externally and further the camera assembly in the present embodiment may be completely isolated sterilely, thereby effectively avoiding or reducing the security risks; since the electrical wire of the camera assembly is not required to pass through the sterile sheath (while the sterile isolation cover may not be a necessity), the difficulty in operation is further reduced, thereby facilitating the use, the disassembly and disposable discarding.

In addition, according to the present embodiment, the electrical connection may be achieved by inserting the male connector with the receptacle, so that a positive effect of simple assembly may be generated; meanwhile, the disposable use and discarding of the receptacle and the external connecting portion as a whole may further generate a positive effect of facilitating the overall disposal.

It can be seen that with the solution involved in the present embodiment, medical scenes where the novel coronavirus, other seriously contagious virus and the like exist may be met, thereby effectively guaranteeing the security and facilitating the use and disposal.

In the further optional solution, based on the structure of resilience compensation, the encapsulation portion of the camera may be located at a required position by using the elastic force, thereby eliminating the effect caused by dimensional errors in manufacturing and assembly on the camera.

At last, it should be noted that the above various embodiments are only used to describe the technical solutions of the present invention, rather than limiting the technical solutions of the present invention. Even through the present invention is described in detail with reference to the foregoing embodiments, those of ordinary skilled in the art should understand that they can still modify the technical solutions recorded in the foregoing various embodiments or equivalently replace some or all of the technical features. However, these modifications or replacements do not make the essence of the corresponding technical solutions deviate from the scope of the technical solutions of the embodiments of the present invention.

What is claimed is:

1. A rigid endoscope, comprising a disposable endoscope body structure and a reusable camera assembly, wherein the endoscope body structure comprises a handle portion, an endoscope body inserting portion and a line connecting portion; the endoscope body inserting portion is directly or indirectly connected to the handle portion, the line connecting portion comprises a receptacle located in the handle portion and an external connecting portion located outside the handle portion, and the receptacle is directly or indirectly connected with the external connecting portion;

wherein the handle portion is provided with a camera assembly access port for the camera assembly to access; after accessing and being assembled to the camera assembly access port, the camera assembly access port is able to be inserted into the receptacle to transmit electrical energy and/or a signal with the external connecting portion by using the receptacle;

wherein the camera assembly comprises a camera, a conducting rod, a grip, a male connector disposed at the grip, and a first electrical wire;

wherein one end of the conducting rod is connected with the grip, and the camera is disposed at the other end of the conducting rod; the first electrical wire penetrates through the conducting rod and the grip, one end of the first electrical wire is directly or indirectly connected with the camera, and the other end of the first electrical wire is directly or indirectly connected with the male connector; and wherein after the camera assembly accesses and is assembled to the camera assembly access port, the male connector is inserted into the receptacle, and the conducting rod penetrates through the endoscope body inserting portion.

2. The rigid endoscope according to claim 1, wherein the grip comprises a grip head and an elastic compensation structure disposed at the grip head;

one end of the elastic compensation structure along a length direction of the conducting rod is directly or indirectly connected with the conducting rod, and the other end of the elastic compensation structure along the length direction of the conducting rod is directly or indirectly connected with the grip head, the grip head being fixed relative to the handle portion after the camera assembly accesses and is assembled to the camera assembly access port;

the elastic compensation structure is configured to directly or indirectly push the conducting rod by using an elastic force after the camera assembly accesses and is assembled to the camera assembly access port, so that the camera is located at a tip of the endoscope body inserting portion.

3. The rigid endoscope according to claim 2, wherein the elastic compensation structure comprises an elastic component, a component cover and a component sleeve, a side wall of the grip head close to the camera being provided with an elastic-component through hole, and the elastic component, the component cover and the component sleeve being all disposed in an inner cavity of the grip head, and the elastic component being connected between the component cover and the component sleeve along the length direction of the conducting rod;

the first electrical wire penetrates through the elastic-component through hole, the component cover and the component sleeve in sequence, the component sleeve is fixed relative to the conducting rod, and the component cover is fixed relative to the grip.

4. The rigid endoscope according to claim 3, wherein the elastic compensation structure further comprises a component seat, the component seat penetrating through the elastic-component through hole, the component cover and the elastic component being both located at an inner side of the component seat, and the component cover covering an end of the component seat deviated from a camera encapsulation portion.

5. The rigid endoscope according to claim 4, wherein the component seat comprises a flat seat body and a cylinder seat body, and an end of the flat seat body being connected with the cylinder seat body; the flat seat body being located outside the grip head, the cylinder seat body penetrating through the elastic-component through hole, and a shape of an outer wall of the cylinder seat body being matched with an inner wall of the elastic-component through hole.

6. The rigid endoscope according to claim 3, wherein the male connector and the elastic-component through hole are disposed at the same side wall of the grip head, and an inner cavity of the grip head is further provided with a male connector circuit board, the male connector circuit board being fixed relative to the side wall, and the first electrical wire being connected with the male connector via the male connector circuit board.

7. The rigid endoscope according to claim 3, wherein the endoscope body structure further comprises a passage tube and a guider that are fixedly connected to the handle portion, the passage tube penetrating through the handle portion, the endoscope body inserting portion being connected to one end of the passage tube, and the guider being connected to the other end of the passage tube;

after the camera assembly accesses and is assembled to the camera assembly access port, the grip accesses the guider, and the conducting rod penetrates through the passage tube and the endoscope body inserting portion in sequence.

8. The rigid endoscope according to claim 3, wherein the endoscope body inserting portion comprises an inserting rod and a head module, the head module being disposed at a tip of the inserting rod, and the other end of the inserting rod being connected with the handle portion;

the head module is provided with a light transmission sheet and an illumination module, and the camera assembly accessing the endoscope body inserting portion may collect images externally through the light transmission sheet.

9. The rigid endoscope according to claim 2, wherein the endoscope body structure further comprises a passage tube and a guider that are fixedly connected to the handle portion, the passage tube penetrating through the handle portion, the endoscope body inserting portion being connected to one end of the passage tube, and the guider being connected to the other end of the passage tube;

after the camera assembly accesses and is assembled to the camera assembly access port, the grip accesses the guider, and the conducting rod penetrates through the passage tube and the endoscope body inserting portion in sequence.

10. The rigid endoscope according to claim 2, wherein the endoscope body inserting portion comprises an inserting rod and a head module, the head module being disposed at a tip of the inserting rod, and the other end of the inserting rod being connected with the handle portion;

the head module is provided with a light transmission sheet and an illumination module, and the camera assembly accessing the endoscope body inserting portion may collect images externally through the light transmission sheet.

11. The rigid endoscope according to claim 1, wherein the male connector is a Type C male connector, and the receptacle is a Type C receptacle.

12. The rigid endoscope according to claim 1, wherein the endoscope body structure further comprises a passage tube and a guider that are fixedly connected to the handle portion, the passage tube penetrating through the handle portion, the endoscope body inserting portion being connected to one end of the passage tube, and the guider being connected to the other end of the passage tube; after the camera assembly accesses and is assembled to the camera assembly access port, the grip accesses the guider, and the conducting rod penetrates through the passage tube and the endoscope body inserting portion in sequence.

13. The rigid endoscope according to claim 1, wherein a material of the conducting rod is a shape memory alloy material.

14. The rigid endoscope according to claim 1, wherein the endoscope body inserting portion comprises an inserting rod and a head module, the head module being disposed at a tip of the inserting rod, and the other end of the inserting rod being connected with the handle portion;

the head module is provided with a light transmission sheet and an illumination module, and the camera assembly accessing the endoscope body inserting portion may collect images externally through the light transmission sheet.

* * * * *